United States Patent
Chen

Patent Number: 6,085,355
Date of Patent: Jul. 11, 2000

[54] HEALTH GOLF GLOVE

[76] Inventor: Yi-Hsi Chen, No. 112, Min Tsu Road, Fu Li Li, Miao Li City, Miao Li Hsien, Taiwan

[21] Appl. No.: 09/276,172

[22] Filed: Mar. 25, 1999

[51] Int. Cl.[7] .................................................. A41D 19/00
[52] U.S. Cl. ................................. 2/161.4; 2/159; 2/162; 2/917; 600/15
[58] Field of Search .......................... 2/159, 161.1, 161.2, 2/161.4, 161.5, 162, 917; 473/205; 600/9, 15

[56] References Cited

U.S. PATENT DOCUMENTS

| | | | |
|---|---|---|---|
| 4,095,587 | 6/1978 | Ishikawa | 128/1.3 |
| 4,905,335 | 3/1990 | Tervola | 2/169 |
| 5,720,046 | 2/1998 | Lopez et al. | 2/159 |
| 5,802,615 | 9/1998 | Wenk | 2/161.2 |
| 5,827,170 | 10/1998 | Gebran | 600/15 |

*Primary Examiner*—Diana Oleksa
*Assistant Examiner*—Katherine Moran
*Attorney, Agent, or Firm*—Browdy and Neimark

[57] ABSTRACT

A golf glove is formed of a palm portion, a back portion opposite to the palm portion, a plurality of finger sheaths, a thumb sheath, and a wrist portion which is provided with a magnetic member having a magnetic field for stimulating the anatomical points of the wrist of a golfer wearing the golf glove so as to promote the health of the golfer.

12 Claims, 2 Drawing Sheets

HEALTH GOLF GLOVE

FIELD OF THE INVENTION

The present invention relates generally to a golf glove, and more particularly to a golf glove capable of enhancing the health of a wearer thereof.

BACKGROUND OF THE INVENTION

The conventional golf gloves are generally intended to provide the users thereof with protection against skin blister or rupture. No "health golf glove" has ever been introduced to the market place today.

SUMMARY OF THE INVENTION

It is therefore the primary objective of the present invention to provide a golf glove for protecting the hand of a golfer.

It is another objective of the present invention to provide a golf glove having means similar in principle to acupuncture for stimulating the anatomical points of wrist of a golfer so as to promote the blood circulation and the body metabolism of the golfer.

The foregoing objectives of the present invention are attained by a golf glove having a body which is formed of a palm portion, a back portion, a plurality of finger sheaths, a thumb sheath, and a wrist portion provide with a magnetic strap for stimulating the anatomical points of the wrist by the magnetic field, so as to promote the blood circulation and the body metabolism of a golfer wearing the glove of the present invention.

The foregoing objectives, features and functions of the present invention will be more readily understood upon a thoughtful deliberation of the following detailed description of two preferred embodiments of the present invention with reference to the accompanying drawings.

DETAILED DESCRIPTION OF THE INVENTION

Figure 1:
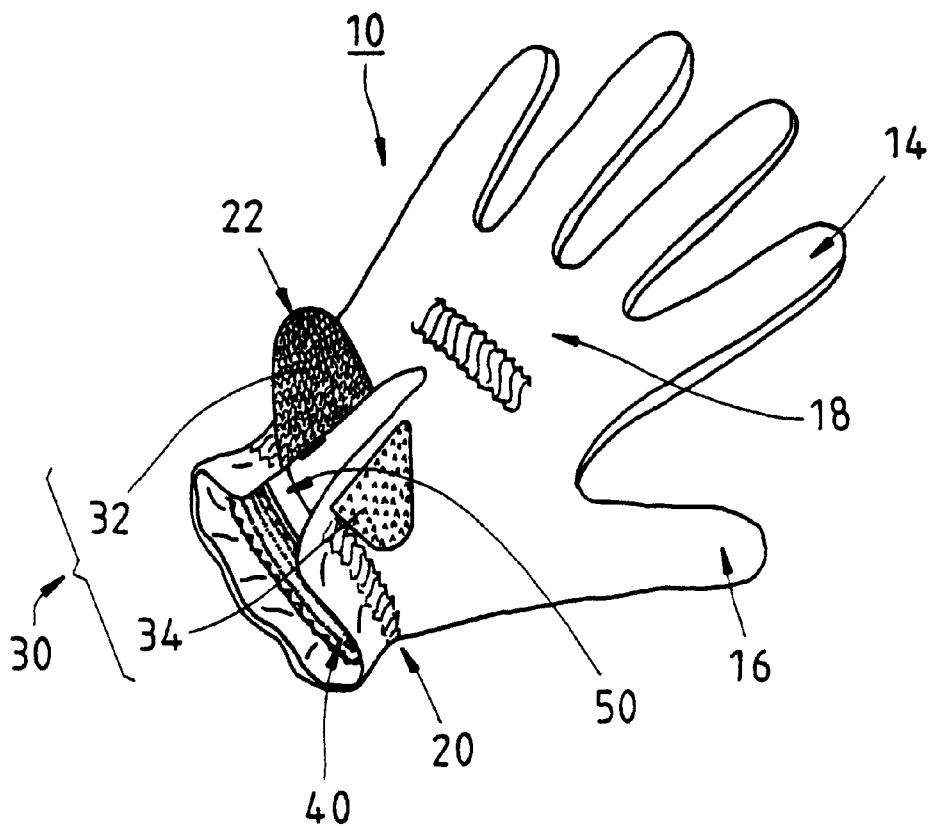
FIG. 1 shows a perspective view of a first preferred embodiment of the present invention.
Figure 2:
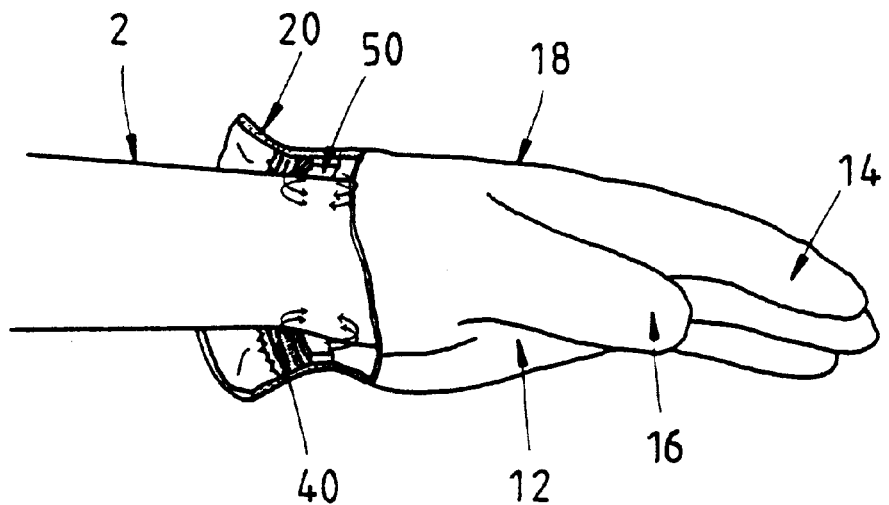
FIG. 2 shows a partial sectional view of the wrist portion of a golf glove of the first preferred embodiment of the present invention in conjunction with a golfer's hand wearing the golf glove.

As shown in FIGS. 1 and 2, a golf glove 10 of the first preferred embodiment of the present invention is formed of a palm portion 12, four finger sheaths 14, a thumb sheath 16, a back portion 18, and a wrist portion 20. The wrist portion 20 is provided with a tongue 22, which is attached to the outer surface contiguous to the back portion 18 and is provided in one side thereof with a hooked portion 32. The back portion 18 is provided with a retaining portion 34 corresponding in location to and engageable with the hooked portion 32. The hooked portion 32 and the retaining portion 34 constitute a fastening member 30 serving to cover securely a golfer's hand 2 with the golf glove 10. The wrist portion 20 is further provided in the inner side thereof with an elastic fastening strap 40 enabling the wrist portion 20 to make an intimate contact with the wrist of the hand 2.

The golf glove 10 of the present invention is characterized by the wrist portion 20 which is provided with a magnetic strap 50 attached to the inner side of the wrist portion 20 such that the magnetic strap 50 is contiguous to the elastic fastening strap 40. The magnetic strap 50 has a width of 12 mm or so, a boundary magnetic flux density ranging between 150 and 400 Gausses, and a magnetic field with a penetration depth ranging between 0.1 mm and 120 mm. As illustrated in FIG. 2, the wrist of the hand 2 is exposed to the magnetic field of the magnetic strap 50, thereby enabling the anatomical points of the wrist to be stimulated by the magnetic field so as to promote the blood circulation and the body metabolism of a golfer wearing the golf glove 10 of the present invention.

Figure 3:
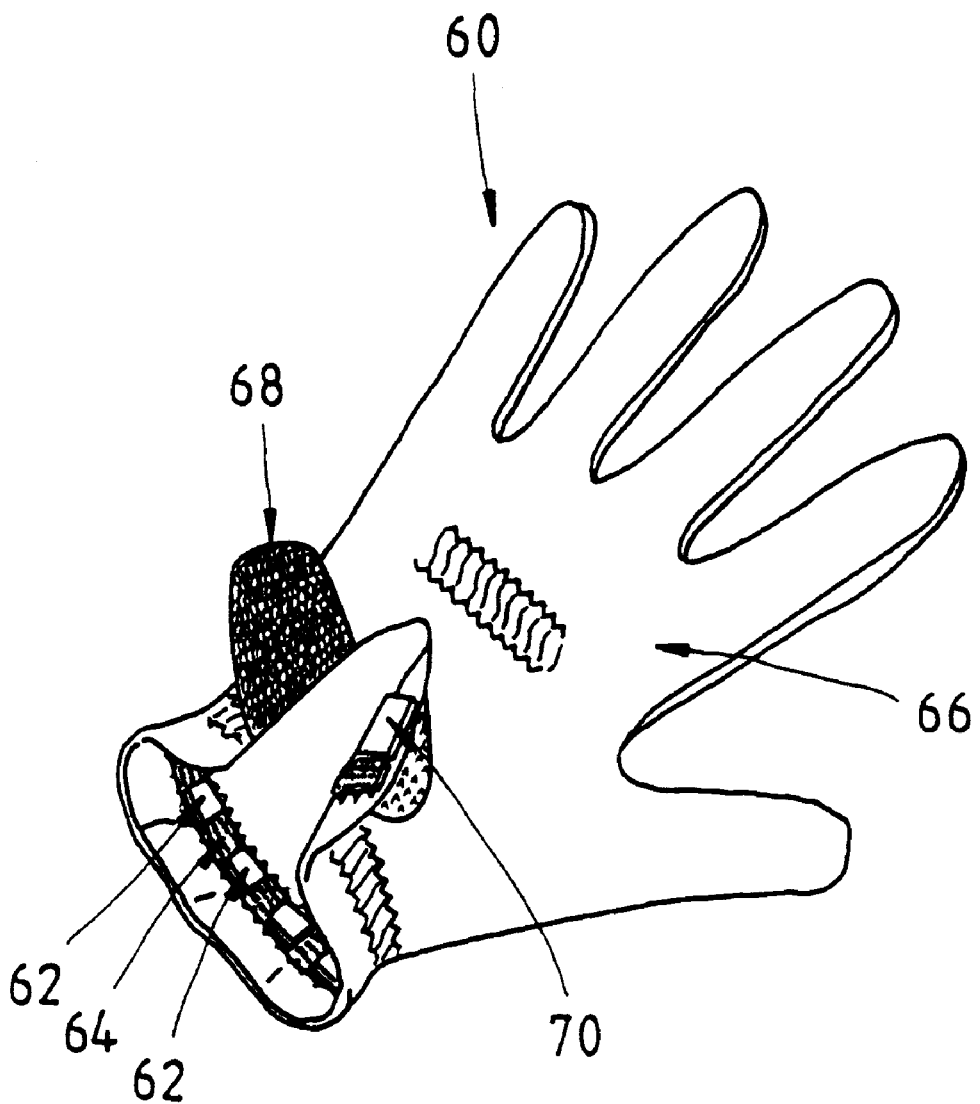
FIG. 3 shows a perspective view of a second preferred embodiment of the present invention.

As shown in FIG. 3, a golf glove 60 of the second preferred embodiment of the present invention is basically similar in construction to the golf glove 10 of the first preferred embodiment described above, except that the golf glove 60 is provided with a magnetic strap which is segmentally attached to an elastic fastening strap 64 at an interval. The segments of the magnetic strap are labeled by a reference numeral "62" in FIG. 3. The golf glove 60 is further provided with a magnetic block 70 which is fastened with the inner side of the back portion 66 such that the magnetic block 70 is opposite to the tongue 68. As a result, the anatomical points of the back side of the palm of a hand wearing the golf glove 60 can be stimulated by the magnetic field of the magnetic block 70.

What is claimed is:

1. A golf glove having a body formed of a palm portion, a back portion opposite to the palm portion, a plurality of finger sheaths, a thumb sheath, and a wrist portion; wherein said wrist portion is provided with at least one magnetic member having a magnetic field for bringing about the effect of promoting the health of a wearer of the golf glove;

wherein said magnetic member is a magnetic strap.

2. The golf glove as defined in claim 1, wherein said magnetic strap has a boundary magnetic flux density ranging between 150 and 400 Gausses.

3. The golf glove as defined in claim 1, wherein said magnetic strap has a magnetic field with a penetration depth in the range of 0.1 mm to 120 mm.

4. The golf glove as defined in claim 1, wherein said magnetic strap is fastened with an inner side of said wrist portion.

5. The golf glove as defined in claim 1, wherein said wrist portion is further provided in an inner side thereof with an elastic fastening strap; and wherein said magnetic member is segmentally attached to said elastic fastening strap at an interval.

6. A golf glove having a body formed of a palm portion, a back portion opposite to the palm portion, a plurality of finger sheaths, a thumb sheath, and a wrist portion; wherein said wrist portion is provided with a tongue fastened therewith for securing the golf glove over a hand, said tongue provided with a releasable fastening member serving to enable said tongue to be releasably fastened with the back portion, said wrist portion further provided with at least one magnetic member having a magnetic field for bringing about the effect of promoting the health of a wearer of the golf glove;

wherein said magnetic member is a magnetic strap.

7. The golf glove as defined in claim 6, wherein said magnetic strap has a boundary magnetic flux density ranging between 150 and 400 Gausses.

8. The golf glove as defined in claim 6, wherein said magnetic strap has a magnetic field with a penetration depth in the range of 0.1 mm to 120 mm.

9. The golf glove as defined in claim 6, wherein said magnetic strap is fastened with an inner side of said wrist portion.

10. The golf glove as defined in claim 6, wherein said wrist portion is further provided in an inner side thereof with an elastic fastening strap; and wherein said magnetic member is segmentally attached to said elastic fastening strap at an interval.

11. The golf glove as defined in claim 6, further comprising a magnetic block which is attached to the inner side of the back portion such that said magnetic block is opposite to said tongue.

12. The golf glove as defined in claim 10 further comprising a magnetic block which is attached to the inner side of the back portion such that said magnetic block is opposite to said tongue.

\* \* \* \* \*